United States Patent [19]

Goldberg et al.

[11] 4,404,924
[45] Sep. 20, 1983

[54] BODY FLUID SUCTION DEVICE INDICATORS

[75] Inventors: Edward M. Goldberg, Glencoe; Seymour Bazell, Skokie, both of Ill.

[73] Assignee: UreSil Company, Morton Grove, Ill.

[21] Appl. No.: 184,235

[22] Filed: Sep. 5, 1980

[51] Int. Cl.³ .................. A61M 1/00; G01L 19/12
[52] U.S. Cl. ............................ 116/270; 92/92; 116/266; 128/760; 604/118
[58] Field of Search ................ 116/264, 270, DIG. 8, 116/210; 128/349 B, 276; 92/92

[56] References Cited

U.S. PATENT DOCUMENTS

| | | | |
|---|---|---|---|
| 654,372 | 7/1900 | West | 116/270 |
| 1,718,602 | 6/1929 | Smith | 128/276 X |
| 1,926,180 | 9/1933 | Rutherford | 116/271 |
| 2,417,449 | 3/1947 | Rubin | 116/DIG. 8 X |
| 2,594,621 | 4/1952 | Derrick | 128/278 |
| 2,607,314 | 8/1952 | Waller | 73/744 X |
| 2,649,091 | 8/1953 | Valencia | 128/278 |
| 2,947,470 | 2/1957 | Ruben et al. | 128/278 |
| 3,002,490 | 10/1961 | Murray | 116/200 |
| 3,018,779 | 1/1962 | Tyler et al. | 128/278 |
| 3,334,628 | 8/1967 | Saemann et al. | 116/268 X |
| 3,407,817 | 10/1968 | Galleher, Jr. | 116/DIG. 8 X |
| 3,481,254 | 12/1969 | Wetherbee, Jr. | 92/92 |
| 3,561,330 | 2/1971 | Rich | 92/92 |
| 3,774,611 | 11/1973 | Tussey et al. | 417/472 X |
| 3,779,243 | 12/1973 | Tussey et al. | 128/278 |
| 3,809,086 | 5/1974 | Schachet et al. | 128/278 |
| 3,871,377 | 3/1975 | Treace | 128/278 |
| 3,889,677 | 6/1975 | Nehring | 128/278 |
| 3,924,519 | 12/1975 | England | 73/731 X |
| 3,983,872 | 10/1976 | Nehring | 128/278 |
| 4,008,717 | 2/1977 | Kowarski | 128/278 X |
| 4,015,478 | 4/1977 | Schmaus | 73/741 |
| 4,022,209 | 5/1977 | Nehring | 128/278 |
| 4,058,123 | 11/1977 | May | 128/278 |
| 4,063,556 | 12/1977 | Thomas | 116/270 X |
| 4,164,938 | 8/1979 | Patton | 73/731 X |
| 4,266,550 | 5/1981 | Bruner | 128/349 B |
| 4,278,089 | 7/1981 | Huck et al. | 128/760 |

*Primary Examiner*—Daniel M. Yasich
*Attorney, Agent, or Firm*—Norman Lettvin

[57] ABSTRACT

A medical suction device is disclosed which includes a vacuum indicator flag. This flag is made up of a flexible tube capped with a plug. The rigidity of the walls of the tube is chosen such that the walls collapse when the pressure inside the tube falls below a predetermined value, thereby allowing the flag to droop. In addition the rigidity of the tube serves to hold the flag upright when the pressure inside the tube rises above a second predetermined value. Thus the state of the flag (upright or drooped) provides a remote indication of the pressure being developed by the suction device. In addition, the suction device uses a constant force coiled ribbon spring to provide substantially constant suction as the suction device is filled. Furthermore, the suction device includes a plurality of separately valved drainage receptacles which can be folded and stored compactly against the drainage device. By sequentially filling each of these receptacles and then removing the respective receptacle from the drainage device only after the respective isolation valve has been closed, relatively large volumes can be drained without opening the suction device to atmosphere.

7 Claims, 4 Drawing Figures

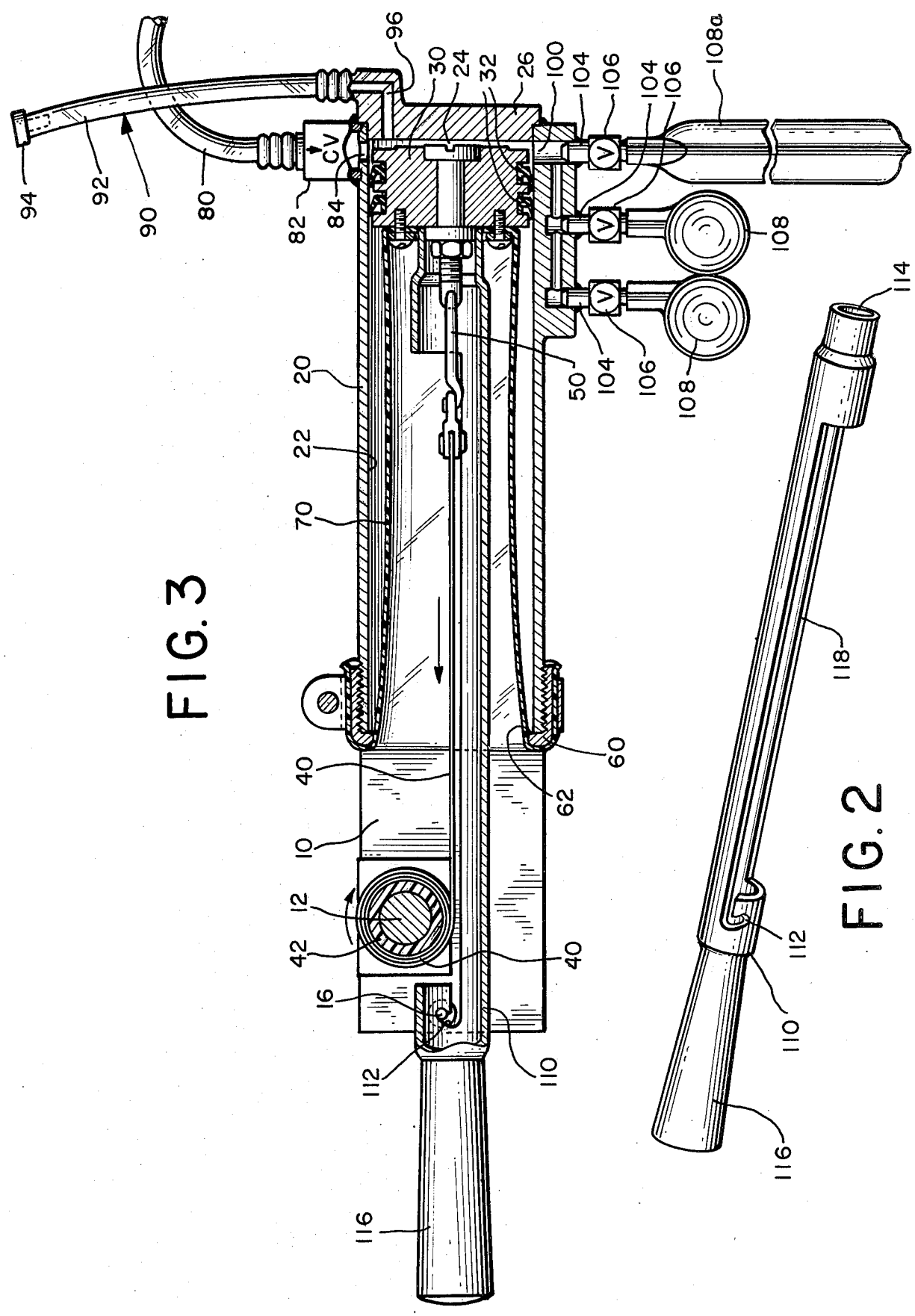

1

BODY FLUID SUCTION DEVICE INDICATORS

BACKGROUND OF THE INVENTION

The present invention relates to an improved suction device used to collect body fluids.

Modern medical practice commonly uses suction devices to improve drainage of fluids from the body of a patient. For example, suction devices are routinely used to speed wound drainage following surgery. One type of wound suction device includes a portable, relatively small suction chamber which is coupled to a source of body fluids. Typically, such chambers are repeatedly charged with a vacuum, filled with body fluids, and then drained during the course of a single drainage treatment. U.S. Pat. Nos. 3,889,677 and 3,779,243 disclose two such portable suction devices.

A potential drawback of many such devices is that it is often difficult to determine from a distance whether the device is developing proper suction. Generally, a portable suction device of the type described above will lose suction when it becomes filled. Unless the loss of suction is promptly noticed and the chamber is emptied to restore suction, proper drainage may be interrupted.

Another potential drawback of many prior art devices relates to the amount of suction developed at various stages in the use of the suction device. Preferably, a suction device should develop a uniform suction throughout its fill cycle, rather than a higher suction when the device is empty and a progressively lower suction as the device fills.

A third drawback of the prior art relates to the contamination of suction devices in use. As explained above, it is customary to fill and empty a suction device repeatedly during a single drainage treatment. Conventional drainage devices must be opened to be drained, and they can therefore become contaminated during use. This contamination can then spread to the patient when drainage is resumed.

SUMMARY OF THE INVENTION

The present invention is directed to an improved suction device which overcomes these and other disadvantages of the prior art.

According to a first aspect of the invention, a suction device includes a vacuum indicator signal or flag. This flag includes a flexible tube in fluid communication with the interior of the suction device. The rigidity of the tube is chosen such that when a high vacuum is present the walls of the tube collapse, thereby reducing the resistance of the tube to lateral bending. Conversely, when a low vacuum or no vacuum is present the tube returns to its rest state, in which the tube exhibits increased resistance to lateral bending. In the preferred embodiment, a mass is attached to the end of the tube such that the tube stands erect when low vacuum is present and the tube droops under the weight of the mass when high vacuum is present. By adjusting the rigidity of the tube and the weight of the mass properly, the tube can be made to droop at the desired vacuum.

This first aspect of the invention provides a simple, direct, reliable and inexpensive indication of the vacuum contained in the suction device. Furthermore, the tube can readily be made of a size and color such that the flag can be seen from a considerable distance to allow remote inspection of the state of the suction device.

According to a second feature of the invention, a suction device includes a substantially constant force spring, such as a negator spring for example, arranged to expand the volume of the suction device such that a substantially constant vacuum is produced as the device fills. Constant force springs of the type disclosed below are reliable and compact. They can be used to create a relatively simple suction device which utilizes any one of several types of vacuum containers.

According to a third aspect of the invention, a suction device is provided with a plurality of drainage receptacles, each of which is connected to the suction device by means of an independently operable isolation valve such that any one of the receptacles can selectively be placed in fluid communication with the suction device. Preferably, each of the receptacles is collapsible for compact storage adjacent the suction device.

This third aspect of the invention provides a closed system suction device having a total drainage capacity which can be much greater than that of the suction device itself. The suction device can be repeatedly filled and drained into the receptacles, and individual receptacles can be removed from the suction device after they have been filled and the respective isolation valves closed, all without ever opening the suction system to atmosphere. In this way, contamination of the suction device and concomitant infection of the patient are reduced.

The invention itself, together with further objects and attendant advantages, will best be understood by reference to the following detailed description taken in connection with the accompanying drawings.

BRIEF DESCRIPTION OF THE DRAWINGS

FIG. 2 is a perspective view of an accessory for use with the embodiment of FIG. 1.

FIG. 3 is a cross-sectional view taken along line 3—3 of FIG. 1.

DETAILED DESCRIPTION OF THE PREFERRED EMBODIMENTS

Figure 1:
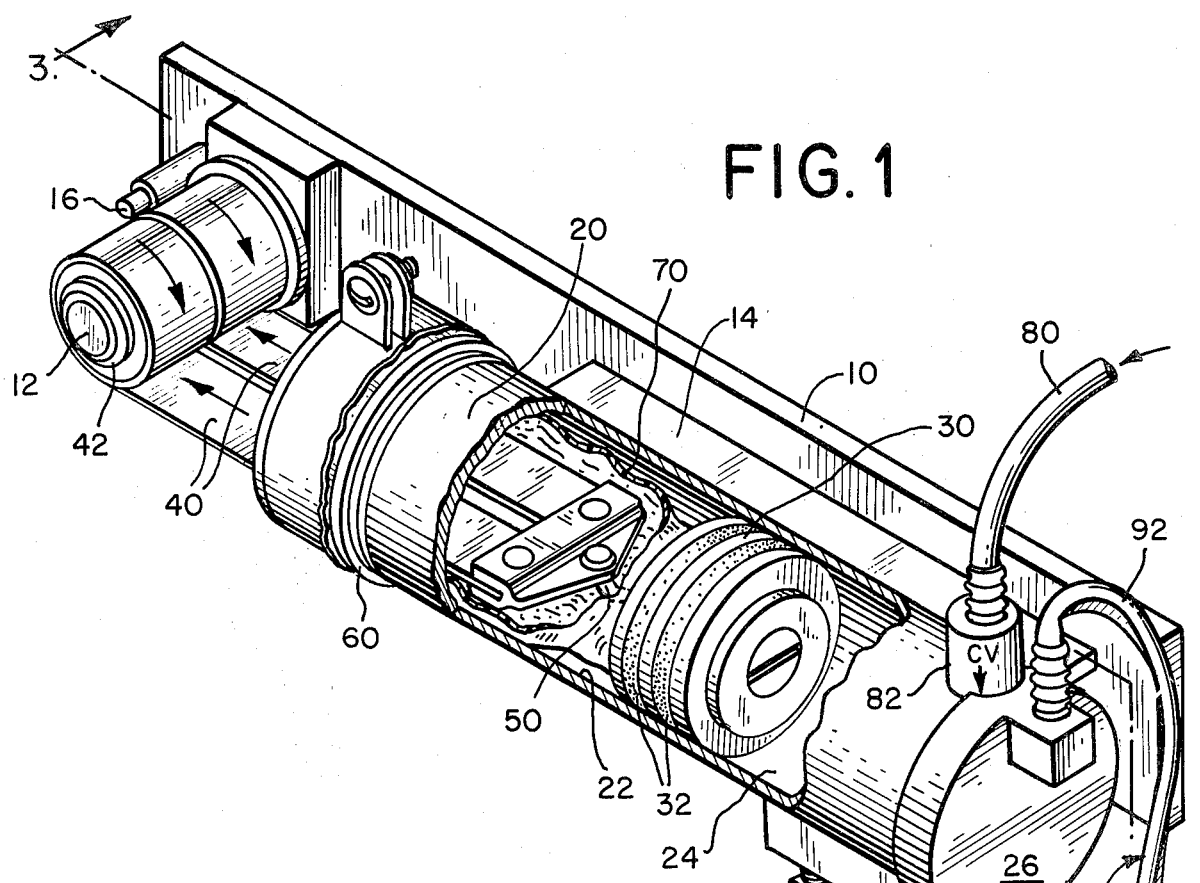
FIG. 1 is a perspective view in partial cutaway of a first preferred embodiment of the suction device of the present invention.

Turning now to the drawings, FIGS. 1-3 represent a first preferred embodiment of the suction device of this invention. As shown in FIGS. 1 and 3, this first preferred embodiment includes a frame 10 which serves as a rigid mount for a shaft 12 and a cylinder 20. Spaced parallel support bars 14 are interposed between and rigidly secured to the frame 10 and the cylinder 20 in order to securely hold the cylinder 20 in place.

A piston 30 having a moveable wall portion is slidably mounted inside the cylinder 20. This piston 30 is provided with two spaced seals 32 which form a vacuum seal between the piston 30 and the cylinder 20. Preferably, these seals 32 are formed of a relatively soft sealing material such as silicone rubber, for example. A pair of constant force, coiled ribbon springs 40 are mounted to a sleeve 42 which is rotatably mounted on the shaft 12. These springs, which are commonly known as negator springs, provide a substantially constant force as they are wound or unwound from the sleeve 42. One end of each of the springs 40 is connected to the piston 30 by means of a flexible coupling 50.

The end of the cylinder 20 nearest the shaft 12 is provided with a collar 60. This collar 60 provides a stop 62 which serves to confine the piston 30 within the cylinder 20. A tubular sleeve 70 of a flexible, elastomeric material is secured between the collar 60 and the piston 30. This sleeve 70 serves to protect the inner walls 22 of the cylinder 20 from exposure to atmosphere and contamination as the piston 30 moves within the cylinder 20. In addition, the dual seals 32 provide an additional barrier which serves to maintain the sterility of the suction chamber 24 defined by the cylinder 20 and the piston 30.

The piston 30 has a constant area surface which is drawn toward the shaft 12 by a substantially constant force provided by the springs 40. Therefore the suction device of FIGS. 1 and 3 provides a substantially constant suction as the piston moves within the cylinder 20.

A conduit 80 is connected to the suction chamber 24 by means of a bore 84. A check valve 82 is interposed in the conduit 80 to insure that fluids do not pass from the suction chamber 24 out the conduit 80. In use, the conduit 80 is connected to a source of body fluids, such as a wound catheter for example. The conduit 80 thus serves to conduct body fluids from a patient into the suction chamber 24.

In addition, an indicator flag 90 is provided. This flag 90 comprises a hollow flexible tube 92, the interior of which is in fluid communication with the suction chamber 24 by means of a bore 96. The distal end of the tube 92 is provided with a plug 94. As will be explained below, the weight of this plug 94 can be important in the functioning of the indicator flag 90.

In addition, a drainage bore 100 is provided which interconnects the suction chamber 24 with a manifold 102. A plurality of conduits 104 are connected to the manifold 102, and each of these conduits 104 is provided with a separately operable isolation valve 106. In addition, each of the conduits 104 is coupled to an individual receptacle 108. Preferably, these receptacles 108 are flexible plastic receptacles which can be folded into a compact volume and stored against the cylinder 20 when not in use. FIGS. 1 and 3 show one of the receptacles 108a in its unfolded state. Each of the isolation valves 106 can be operated independently of the others, and each valve 106 is movable between a closed state, in which the manifold 102 is isolated from the respective receptacle 108, and an open state, in which the respective receptacle 108 and the manifold 102 are interconnected.

Preferably the suction chamber 24, the indicator flag 90, and the manifold 102 with attached receptacles 108 form a closed, sterile unit. As explained above, the sleeve 70 and the seals 32 contribute to maintaining the sterility of this unit. In this preferred embodiment, the cylinder 20 is made of a rigid plastic such as the plastics commonly used to form plastic syringes. In addition the tube 92 of the indicator flag 90 is formed of a silicone rubber which defines a flexible wall having a resilience sufficient to hold the tube 92 and the plug 94 upright, as shown in FIG. 3, when the pressure inside the suction chamber 24 is greater than a first predetermined amount. However, when the pressure within the suction chamber 24 is less than a second predetermined amount, the atmospheric pressure pushes the walls of the tube 92 together, thereby reducing the lateral rigidity of the tube 92. In these circumstances the weight of the plug 94 acts to pull the tube 92 downward, away from its erect position of FIG. 3. FIG. 1 provides a perspective view of the indicator flag 90 as it appears when the pressure in the suction chamber 24 is less than the second predetermined amount.

Preferably, the springs 40 are chosen such that the suction developed within the suction chamber 24 is in the range 75-90 mm Hg below atmospheric pressure. Associated Springs, Barnes Group, Inc., Bristol Connecticut is one supplier for the constant face springs 40.

In this preferred embodiment, the indicator flag 90 assumes the upright position, as shown in FIG. 3, when the suction in the chamber 24 is less than about 20 mm Hg below atmospheric pressure and the flag 90 assumes the position of FIG. 1 when the suction in the chamber 24 is greater than about 40 mm Hg below atmospheric pressure. Between 20 and 40 mm Hg, the indicator flag 90 assumes intermediate positions, thereby providing additional information as to the degree of suction in the chamber 24. It can thus be seen from the above that the indicating device is designed for operation at subatmospheric pressures.

In this preferred embodiment the flag 90 comprises a tube made of silicone rubber having an outer diameter of 5/16 inch, a wall thickness of 1/32 inch, a length of about 4¾ inches, and a hardness of 75 durometer Shore A scale. Preferably the plug 94 has a mass of between one and one and one-half grams. Of course, the rigidity of the walls of the tube 92, the composition of the tube 92, and the weight of the plug 94 can be readily adjusted to cause the flag 90 to change state at other negative pressures, as desired.

FIG. 2 shows a perspective view of a hand tool 110 which is used in operating the suction device of FIGS. 1 and 3. This hand tool 110 includes an opening 112, a cut-out region 118, an end section 114, and a handle 116.

Referring now particularly to FIG. 3, the operation of this first preferred embodiment can now be described. To prepare the suction device of FIG. 3 for use, the hand tool 110 is placed with the end section 114 against the piston 30. The handle 116 is then grasped and force is manually exerted to extend the springs 40 and to push the piston 30 against the end 26 of the cylinder 20. Once the spring 40 is fully extended, the hand tool 110 can be locked in position by placing the tab 16 within the opening 112 of the hand tool 110. The conduit 80 can then be connected to a wound catheter or another source of body fluids to be drained under suction. In this situation, when there is relatively high pressure within the suction chamber 24, the indicator flag 90 stands upright as shown in FIG. 3.

In order to begin drainage, each of the three isolation valves 106 is closed, the conduit 80 is connected to a source of body fluids, and the hand tool 110 is removed. The springs 40 then exert a substantially constant force tending to withdraw the piston 30 away from the end 26 of the cylinder 20. This creates a substantially constant suction tending to draw body fluids through the conduit 80 into the suction chamber 24. FIG. 1 shows a perspective view of this embodiment of the invention in use. Note that the indicator flag 90 has collapsed, thereby indicating the presence of adequately low pressure within the suction chamber 24.

Once the piston 30 has withdrawn to the maximum extent possible against the stop 62, the pressure inside the suction chamber 24 will rise, and the indicator flag 90 will return to the upright position shown in FIG. 3. In order to drain the suction chamber 24 and to prepare it for further use, a selected one of the isolation valves 106 is opened, and the hand tool 110 is then used to push the piston 30 towards the end 26 of the cylinder 20. This forces body fluids out of the suction chamber 24 into the selected receptacle 108. The check valve 82 prevents drained fluids from being pushed back up the conduit 80 into the patient. Once the piston 30 has been returned to its extended position against the end 26 of the cylinder 20, the drainage procedure can be resumed. Preferably, all of the isolation valves 106 are closed while suction is applied to the conduit 80 to prevent body fluids from being drawn back into the suction chamber 24 from the receptacle 108.

It will be understood that the total drainage capacity of the embodiment of FIGS. 1 and 3 can be much greater than the capacity of the suction chamber 24. For example, the suction chamber 24 can be provided with a total capacity of two hundred of four hundred or six hundred milliliters and each of the receptacles 108 can be provided with a total capacity of one liter. Since the receptacles 108 can be folded into a compact volume for storage, the total size of the embodiment of FIGS. 1 and 3 is small. Nevertheless, a large volume of body fluids can be drained under suction without ever opening the suction chamber 24 to atmosphere.

When a receptacle 108 has been filled in the manner described above, the respective isolation valve 106 can be closed, and then the entire receptacle 108 can be severed from the suction device for disposal, while leaving the respective isolation valve 106 connected to the suction device such that the suction chamber 24 is never opened to atmosphere. Drainage can then continue by opening another isolation valve 106 and unfolding the respective receptacle 108 to receive body fluids. Thus, a high volume suction device is provided which is relatively low in bulk and yet which can be used without opening the suction chamber to atmosphere. In this way contamination of the suction chamber 24 and concomitant infection of the patient can be reduced.

Figure 4:
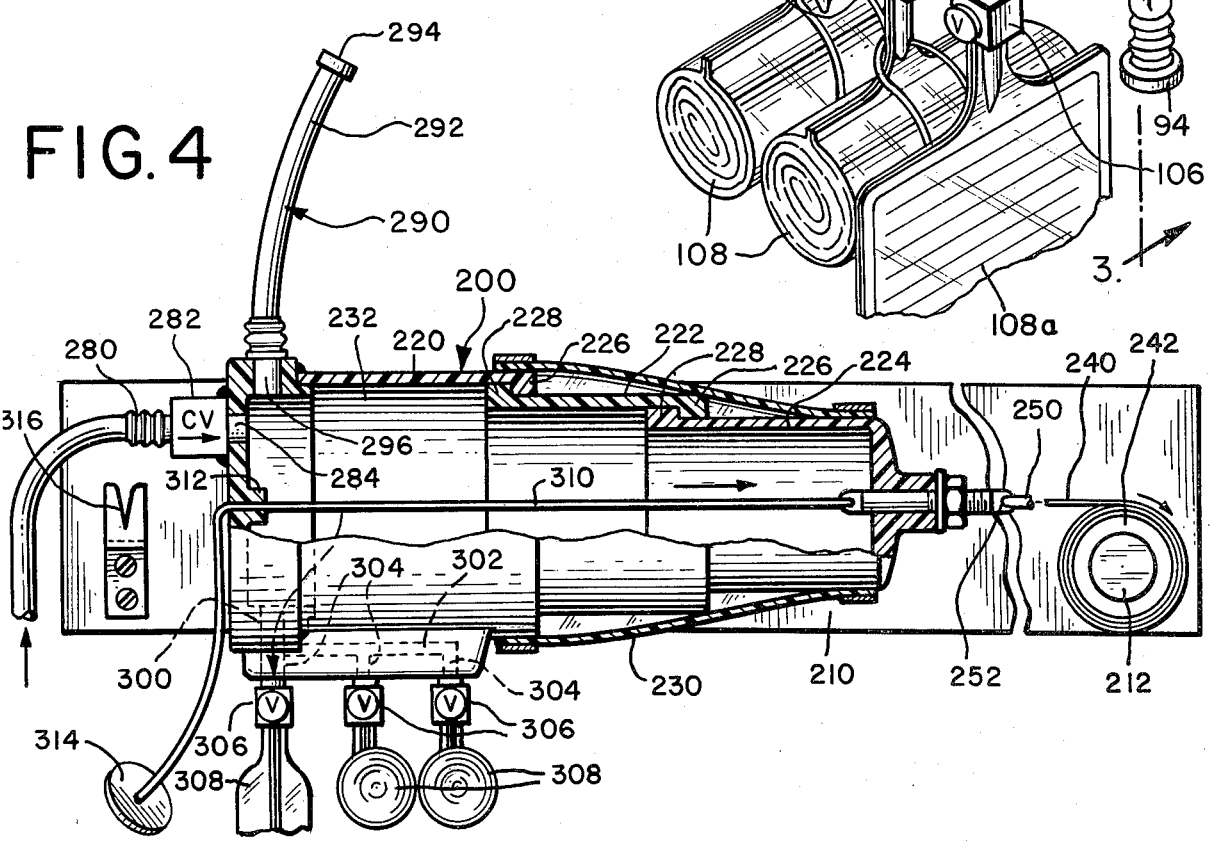
FIG. 4 is a cross-sectional view of a second preferred embodiment of the suction device of the present invention.

Turning now to FIG. 4, a second preferred embodiment 200 of the present invention includes a frame 210 which serves as a rigid mount for a shaft 212 and a pair of spaced parallel support bars (not shown, but similar to the support bars 14 of FIG. 1). A cylinder 220 is rigidly mounted to the support bars 214 and thereby to the frame 210. A pair of smaller concentric cylinders 222,224 are slidably mounted within the cylinder 220. Each of the cylinders 220,222 defines an annular lip 226, and each of the cylinders 222,224 defines a mating flange 228. The lips 226 and the flanges 228 cooperate to form stops to define the maximum extension of the cylinders 222,224 within the cylinder 220. A flexible plastic cover 230 is bonded between cylinder 220 and cylinder 224 to seal the suction chamber 232 defined by the interior of the cylinders 220,222,224. A pair of constant force springs 240 are coiled about a sleeve 242 which is rotatably mounted on the shaft 212. These springs 240 are mounted by means of a flexible coupling 252 to the end of the innermost cylinder 224. As in the first preferred embodiment of FIGS. 1 and 3, the spring 240 provides a substantially constant force in the direction of the shaft 212.

As in the first preferred embodiment, this second preferred embodiment 200 includes a conduit 280 which is coupled by means of a check valve 282 and a bore 284 to the suction chamber 232. In addition, an indicator flag 290 comprising a flexible tube 292 and a plug or mass 294 is in fluid connection with the suction chamber 232 by means of a bore 296. Moreover, a bore 300 serves to connect a manifold 302 with the suction chamber 232, and this manifold 302 is connected by a plurality of conduits 304 with respective isolation valves 306 and receptacles 308.

In addition, a tension member 310, which in this preferred embodiment is made up of a monofilament nylon cord, is attached to the innermost cylinder 224 inside the suction chamber 232. This tension member 310 extends through a seal 312 to the exterior of the suction device. The distal end of the tension member 310 is provided with a handle 314, and a V-shaped groove 316 is defined in a rib secured to the frame 210.

This second preferred embodiment is prepared for use by manually pulling the handle 314 of the tension member 310 to move the inner cylinder 224 towards the indicator flag 290, and thereby to extend the springs 240. Once the volume of the suction chamber 232 has been reduced to the smallest volume possible, the tension member 310 can be wedged into position in the V-shaped groove 316 in order to maintain the springs 240 in the extended position. Suction can be applied to the conduit 280 by merely releasing the tension member 310 from the V-shaped groove 316, thereby allowing the springs 240 to act to expand the volume of the suction chamber 232. As before, the indicator flag 290 provides a remote visual indication of the pressure inside the suction chamber 232. If desired, a protective cover can be installed around the exterior portion of the tension member 310 in order to reduce the chances of contamination of the suction chamber 232. The seal 312 preferably provides a wiping action to reduce contamination which may enter the suction chamber 232 on the tension member 310.

From the foregoing, it should be apparent that an improved suction device has been disclosed which provides a number of important advantages. First, this suction device includes a simple, reliable indicator of the suction being developed by the suction device. In the preferred embodiment this indicator is a tubular flag having a length of three or more inches which droops markedly when the suction is within the desired range. This visual indicator can easily be monitored across a room, and it therefore facilitates proper monitoring of the suction device.

Second, the embodiments described above utilize a simple and reliable constant force, coiled ribbon spring to provide substantially constant suction throughout the filling of the suction chamber. Constant suction provides the important advantage that the level of suction can be chosen and maintained at its optimum level in order to promote drainage optimally.

A third important advantage of the embodiments described above is that they allow closed system suction drainage. As explained above, a relatively small capacity suction chamber can be used in combination with a number of separately valved drainage receptacles. The suction device can be repeatedly filled and emptied into the various receptacles, which can be separated from the suction device as they become filled. Because the entire suction device is a single, sealed, sterile unit, there is no need to attach receptacles, or to reattach fresh receptacles to the drainage device. By avoiding this intermittent opening of portions of the drainage device to atmosphere, contamination of the drainage device and therefore infection of the patient are reduced.

Of course, it should be understood that various changes and modifications to the preferred embodiments described above will be apparent to those skilled in the art. For example, coiled constant force springs of the type which exert a pushing rather than a pulling force can be used to provide a constant suction device of the type described above. In addition, it may not be necessary to utilize a mass such as the plug 94 in all embodiments to obtain the desired drooping characteristics of the indicator flag 90. Furthermore, the size and proportion of the embodiments described above can be varied as needed to suit individual applications. Such changes and modifications do not depart from the spirit and scope of the present invention. It is therefore intended that the following claims be interpreted to cover all such changes and modifications.

We claim:

1. A suction device for receiving body fluids comprising:
   container means including a constant force moveable wall means for defining a suction chamber adapted to maintain a subatmospheric pressure and to receive body fluids;
   a vacuum indicator comprising a flexible tube which is closed at one end by a preselected mass, said tube movable between a rest state, in which the interior volume of the tube has a first value, and a collapsed state, in which the interior volume of the tube is substantially less than the first value;
   means for mounting the tube to the container means such that the interior volume of the tube is in fluid communication with the suction chamber;
   the flexibility of said tube being chosen such that the tube collapses to the collapsed state when a subatmospheric pressure less than a first predetermined value is induced in the suction chamber, and the tube returns to the rest state when the pressure in the container means rises to a value greater than a second predetermined value, greater than the first predetermined value, such that the tube provides a visual indication of the pressure in the suction chamber.

2. The invention of claim 1 wherein the closed end of the tube projects away from the container means when the tube is in the rest state and wherein the flag further comprises the mass secured to the closed end of the tube, the weight of said mass being chosen such that the tube is erect when the tube is in the rest state and the tube is deflected by the mass when the tube is in the collapsed state.

3. The invention of claim 2 wherein the tube is formed of an elastomeric material.

4. The invention of claim 2 wherein the mass comprises a stopper which fits in the tube to seal the closed end of the tube.

5. The invention of claim 1 wherein the transition between the rest state and the collapsed state is gradual such that the flag provides a visual indication of the pressure between the first and second predetermined values.

6. A suction device for receiving body fluids comprising:
   container means including a constant force moveable wall means for defining a suction chamber adapted to maintain a subatmospheric pressure and to receive body fluids;
   means for connecting the suction chamber to a source of body fluids;
   a flexible plastic tube having an open end and a closed end that is closed by a preselected mass;
   means for connecting the open end of the tube to the container means such that the interior of the tube is in fluid communication with the suction chamber and the tube extends away from the container means; and
   a weight secured to the tube at a point remote from the open end;
   the rigidity of the tube and the size of the weight chosen being such that the tube stands erect when a pressure greater than a first predetermined amount is induced inside the suction chamber and the tube collapses and droops when a subatmospheric pressure less than a second predetermined amount is induced inside the suction chamber, thereby providing a clear visual indication of the pressure inside the suction chamber.

7. A suction device for receiving body fluids comprising:
   container means including a constant force moveable wall means for defining a suction chamber adapted to maintain a subatmospheric pressure and to receive body fluids;
   a flexible plastic tube having an open end and a closed end that is closed by a preselected mass;
   means for connecting the open end of the tube to the container means such that the interior of the tube is in fluid communication with the suction chamber and the tube extends away from the container means; and
   a weight secured to the tube at a point remote from the open end;
   the rigidity of the tube and the size of the weight chosen such that the tube stands erect when a pressure greater than a first predetermined amount is induced inside the suction chamber and the tube collapses and droops when a subatmospheric pressure less than a second predetermined amount is induced inside the suction chamber, thereby providing a clear visual indication of the pressure inside the suction chamber.

* * * * *